United States Patent
Goehl et al.

(10) Patent No.: US 7,621,884 B2
(45) Date of Patent: Nov. 24, 2009

(54) TUBE FOR MEDICAL APPLICATIONS AND CIRCUIT INCORPORATING SUCH TUBE

(75) Inventors: Hermann Goehl, Bisingen (DE); Martin Hanna, Rottenburg (DE); Marcello Malagoli, Modena (IT); Annalisa Delnevo, Sant'Agata Bolognese (IT)

(73) Assignee: Gambro Lundia AB (SE)

( * ) Notice: Subject to any disclaimer, the term of this patent is extended or adjusted under 35 U.S.C. 154(b) by 391 days.

(21) Appl. No.: 10/508,328

(22) PCT Filed: Mar. 7, 2003

(86) PCT No.: PCT/IB03/00934

§ 371 (c)(1),
(2), (4) Date: Sep. 20, 2004

(87) PCT Pub. No.: WO03/077966

PCT Pub. Date: Sep. 25, 2003

(65) Prior Publication Data

US 2005/0148924 A1 Jul. 7, 2005

(30) Foreign Application Priority Data

Mar. 20, 2002 (IT) .......................... MI2002A0589
Mar. 20, 2002 (IT) .......................... MI2002A0590

(51) Int. Cl.
*A61M 37/00* (2006.01)
*A61M 1/00* (2006.01)
*B29C 47/00* (2006.01)
*F16L 11/00* (2006.01)
*F16L 9/14* (2006.01)

(52) U.S. Cl. ................ 604/4.01; 604/5.01; 604/6.15; 604/27; 156/244.11; 156/244.13; 156/244.19; 156/296; 422/44; 138/118; 138/137; 138/141

(58) Field of Classification Search ................ 604/6.09, 604/6.11; 264/171.1; 425/130, 133.1; 106/270; 156/244.11, 244.13, 244.19, 296; 138/118, 138/137, 141
See application file for complete search history.

(56) References Cited

U.S. PATENT DOCUMENTS 3,310,604 A * 3/1967 Steingiser et al. ............ 525/125

(Continued)

FOREIGN PATENT DOCUMENTS

CA 2106001 8/1993

(Continued)

OTHER PUBLICATIONS http://www.gallinausa.com/pdfs/polycarb.chemical.resistance.pdf (Information from Dow Plastics, polycarbonate. Accessed Jun. 24, 2007).*

(Continued)

*Primary Examiner*—Tatyana Zalukaeva
*Assistant Examiner*—Adam Marcetich
(74) *Attorney, Agent, or Firm*—Finnegan, Henderson, Farabow, Garrett & Dunner L.L.P.

(57) ABSTRACT

A tube for medical applications comprises a chlorine-free material and has a layer defining an outer surface of the tube. The tube is manufactured from a polymer material having a solubility parameter within the range $9.9 \pm 1.5$ $(cal/cm^3)^{1/2}$.

18 Claims, 4 Drawing Sheets

U.S. PATENT DOCUMENTS

| | | | |
|---|---|---|---|
| 4,229,299 A * | 10/1980 | Savitz et al. | 210/85 |
| 4,436,620 A * | 3/1984 | Bellotti et al. | 210/90 |
| 4,516,977 A * | 5/1985 | Herbert | 604/415 |
| 4,540,413 A * | 9/1985 | Russo | 604/320 |
| 4,753,222 A * | 6/1988 | Morishita | 600/140 |
| 4,948,643 A | 8/1990 | Mueller | |
| 5,059,375 A | 10/1991 | Lindsay | |
| 5,116,652 A | 5/1992 | Alzner | |
| 5,264,488 A | 11/1993 | Takeuchi et al. | |
| 5,274,035 A | 12/1993 | Chundury | |
| 5,281,670 A | 1/1994 | Lee et al. | |
| 5,294,672 A | 3/1994 | Peiffer | |
| 5,324,760 A | 6/1994 | Hopperdietzel | |
| 5,352,201 A | 10/1994 | Jemmott | |
| 5,356,709 A | 10/1994 | Woo et al. | |
| 5,399,401 A | 3/1995 | Powell | |
| 5,439,454 A | 8/1995 | Lo et al. | |
| 5,496,291 A | 3/1996 | Spencer | |
| 5,529,821 A | 6/1996 | Ishikawa et al. | |
| 5,533,992 A | 7/1996 | Patel et al. | |
| 5,538,510 A * | 7/1996 | Fontirroche et al. | 604/265 |
| 5,562,127 A | 10/1996 | Fanselow et al. | |
| 5,601,889 A | 2/1997 | Chundury et al. | |
| 5,620,760 A | 4/1997 | Galimberti et al. | |
| 5,738,923 A | 4/1998 | Ko et al. | |
| 5,741,452 A | 4/1998 | Ryan et al. | |
| 5,928,744 A * | 7/1999 | Heilmann et al. | 428/36.6 |
| 6,261,655 B1 * | 7/2001 | Rosenbaum et al. | 428/36.7 |
| 6,461,696 B1 * | 10/2002 | Ling et al. | 428/34.5 |
| 7,112,357 B2 * | 9/2006 | Miller et al. | 428/36.92 |
| 2001/0013499 A1 * | 8/2001 | Morano et al. | 215/11.6 |
| 2003/0076693 A1 * | 4/2003 | Pameijer et al. | 362/573 |
| 2003/0138582 A1 * | 7/2003 | Miller et al. | 428/36.9 |

FOREIGN PATENT DOCUMENTS

| | | |
|---|---|---|
| EP | 0 396 950 B1 | 11/1990 |
| EP | 0 417 552 B1 | 3/1991 |
| EP | 0 518 061 B1 | 12/1992 |
| EP | 0 571 787 A1 | 12/1993 |
| EP | 0 576 868 B1 | 1/1994 |
| EP | 0 659 442 A1 | 6/1995 |
| EP | 0 729 761 A2 | 9/1996 |
| EP | 0 729 762 A3 | 9/1996 |
| EP | 0 766 972 B1 | 4/1997 |
| EP | 1 136 086 A2 | 9/2001 |
| EP | 1 170 116 A1 | 1/2002 |
| EP | 1 180 372 A1 | 2/2002 |
| WO | WO 92/11820 * | 6/1992 |
| WO | WO 92/11820 * | 7/1992 |
| WO | WO 93/23093 | 11/1993 |
| WO | WO 00/76564 A1 | 12/2000 |
| WO | WO 02/18488 A1 | 3/2002 |

OTHER PUBLICATIONS http://en.wikipedia.org/wiki/Polyurethane (Online encyclopedia, "Polyurethane." Accessed Jul. 2, 2007).*

* cited by examiner

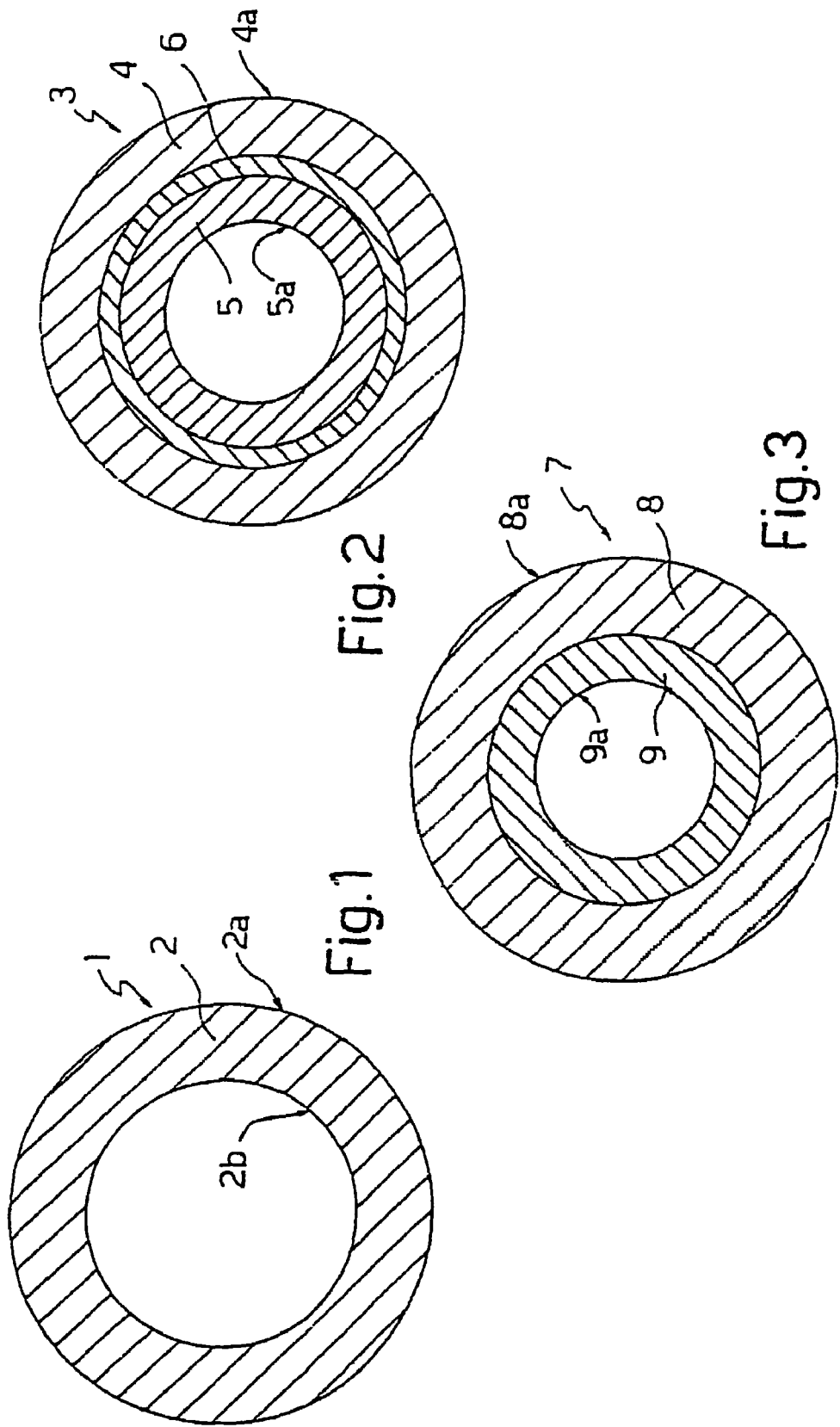

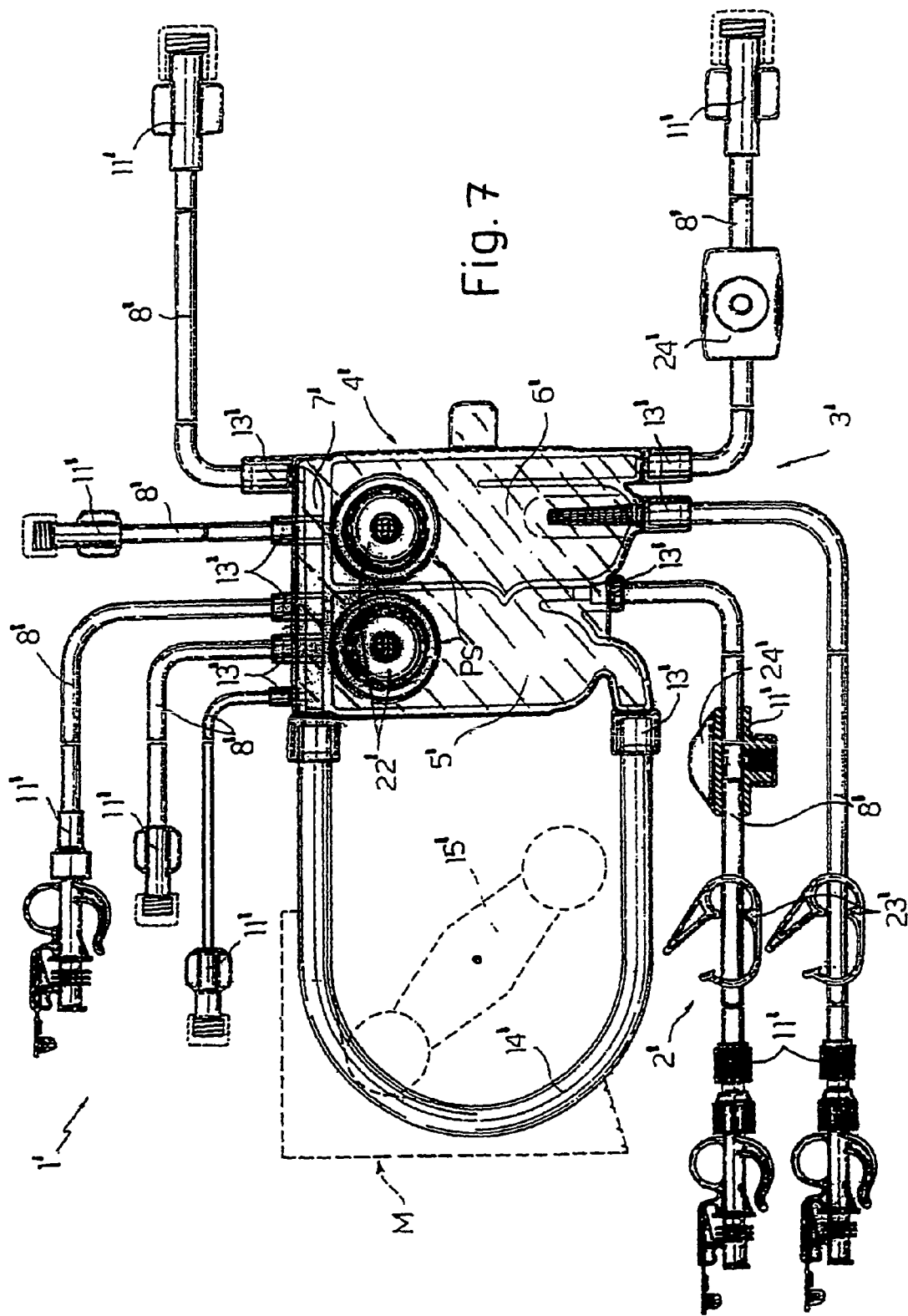

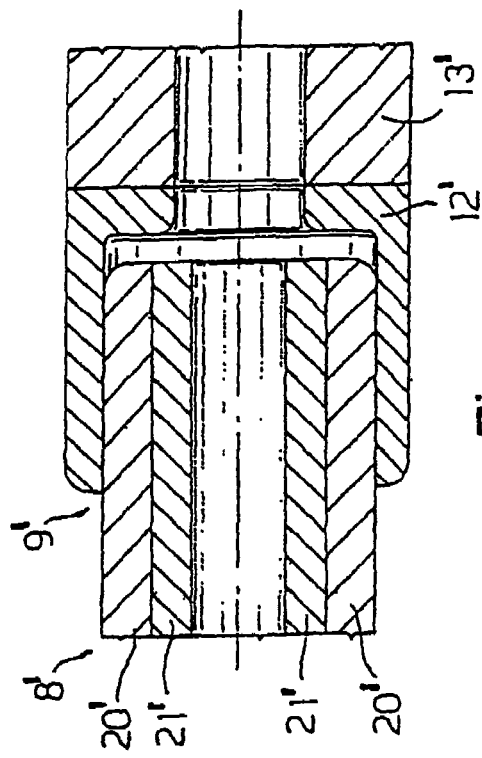
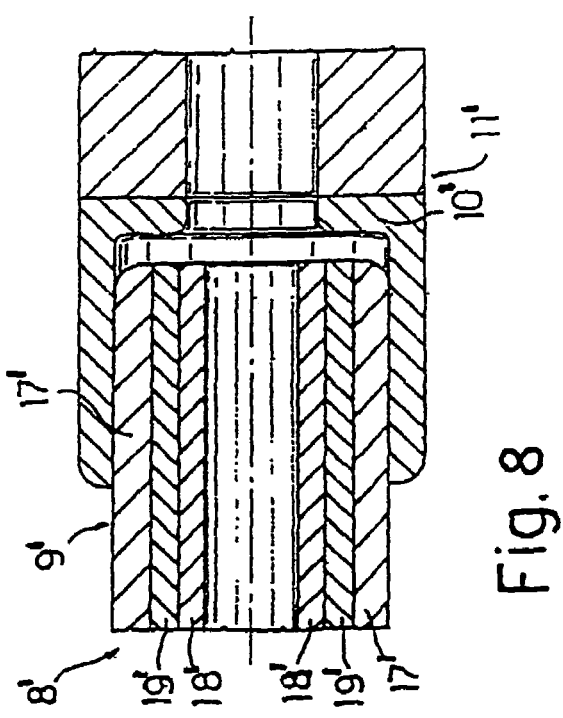
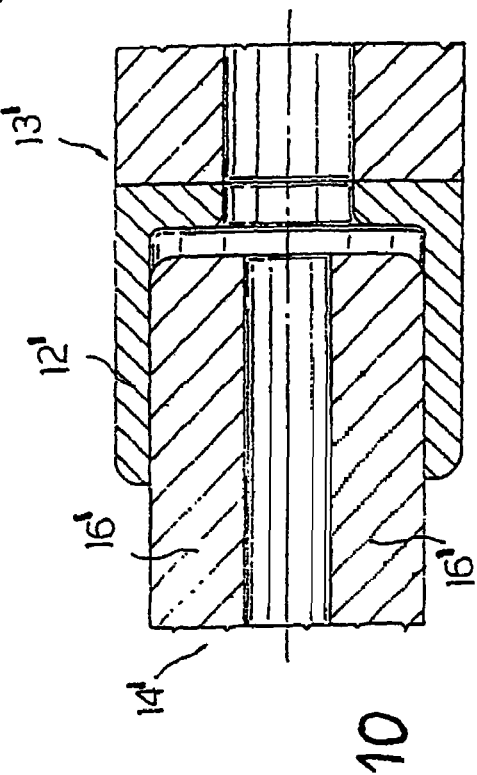

TUBE FOR MEDICAL APPLICATIONS AND CIRCUIT INCORPORATING SUCH TUBE

BACKGROUND OF THE INVENTION

This invention relates to a tube for medical applications and to an extracorporeal circuit for blood circulation.

In particular this invention relates to a tube for medical applications used to construct the extracorporeal circuit of a machine for the purification of blood.

Moreover the invention relates to an extracorporeal circuit for blood circulation of a machine for blood purification, to which the present invention will make specific reference without thereby relinquishing its general applicability.

A known machine for the purification of blood comprises an extracorporeal blood circuit and a blood processing unit, commonly known as a filter, which comprises a compartment through which blood passes when in use and a compartment to receive the undesired substances contained in the blood. The two compartments of the filter are separated by a semipermeable membrane.

An extracorporeal blood circuit comprises, in addition to the venous branch and the arterial branch, connectors for the needles, connectors for sensors, a casing forming two expansion chambers, and various branches connected to the expansion chamber. In practice, each extracorporeal circuit comprises first components made from flexible material, such as the tubes that form the arterial branch and the venous branch, and second components made from rigid material such as the connectors and the casing.

The materials chosen for making the first and second components are generally polymers, which must have specified general characteristics, such as transparency and mechanical strength. In addition, the materials used for making the tubes must have a specified elasticity and a specified resistance to kinking, in other words the capacity to prevent the blocking of the tube when the tube is bent around one point of the tube itself.

PVC has all the abovementioned characteristics and is therefore generally used for making the tubes.

Although PVC has the undoubted advantages cited above, it also has drawbacks associated with the disposal of the extracorporeal circuit. For example, the first and second components of the extracorporeal circuit come into contact with the blood during the blood treatment, and must be incinerated. The incineration of PVC causes the emission of substances that are harmful both to the environment and to the human body. The substances emitted during incineration include particularly harmful ones such as hydrochloric acid (HCl), polychlorinated dibenzodioxins, and furan toxins.

Another disadvantage of the use of PVC relates to the presence of di(2-ethylhexyl)phthalate (DEHP), which is used as a plasticizer in combination with the PVC and is suspected of acting as a carcinogen.

Since it became a requirement to avoid polymers containing chlorine, various chlorine-free polymers with similar physical and mechanical characteristics to PVC have been proposed. However, these chlorine-free polymers have a number of disadvantages arising from the operations of joining the different components of the extracorporeal circuit.

In particular, these disadvantages arise from the fact that, in general, the joining operations are carried out by applying either thermal energy or radio-frequency energy to the parts included in the joints. As a result of the heat that they inevitably produce, these joining procedures can seriously damage the tubes, to such an extent that their function is adversely affected. This is because the heat required for welding is frequently considerable, since the first and second components must withstand without degradation the high sterilization temperatures required by the regulations concerning material for biomedical use. Consequently, the application of a large quantity of heat, sufficient for effective welding, to small components cannot be easily controlled.

SUMMARY OF THE INVENTION

A purpose of this invention is to provide a tube for medical applications which in addition to being chlorine-free is suitable for the simple and economic manufacture of an extracorporeal circuit for a machine for the purification of blood.

An object of the present invention is to provide an extracorporeal circuit for blood circulation comprising first components and second components welded to each other in a simple and economical way.

In accordance with this invention a tube for medical applications comprising a chlorine-free material is provided, the tube comprising at least one layer of polymer material and being characterized in that the said layer defines an outer surface and is manufactured from a polymer material having a solubility parameter within the range $9.9 \pm 1.5$ $(cal/cm^3)^{1/2}$ in order to be soluble in a solvent having a solubility parameter lying within the range $9.9 \pm 1.5$ $(cal/cm^3)^{1/2}$.

According to the present invention, an extracorporeal circuit for circulation according to the description in the attached claims is provided.

The solubility parameter to which this invention refers is that found by the method described in the ASTM D 3132 standard.

Preferably, the first and second portions have solubility parameters lying in a range from 9.4 to 10.4 $(cal/cm^3)^{1/2}$.

Preferably, the first and second portions are soluble in cyclohexanone.

BRIEF DESCRIPTION OF THE DRAWINGS

The examples which follow are solely of an illustrative and non-restrictive nature for better understanding of the invention, and refer to the appended figures in which:

FIG. 1 is a view in cross section of a medical tube according to a first embodiment of this invention, FIG. 2 is a view in cross section W medical tube according to a second embodiment of this invention, FIG. 3 is a view in cross section of a medical tube according to a third embodiment of this invention.

FIG. 7 is a front elevation, with parts removed for clarity and parts shown in section, of an extracorporeal circuit for blood circulation associated with a blood purification machine; and FIGS. 8, 9 and 10 are sectional views, with parts removed for clarity, of tubes welded to corresponding connectors of the extracorporeal circuit of FIG. 7.

DETAILED DESCRIPTION OF THE EMBODIMENTS

Figure 4:
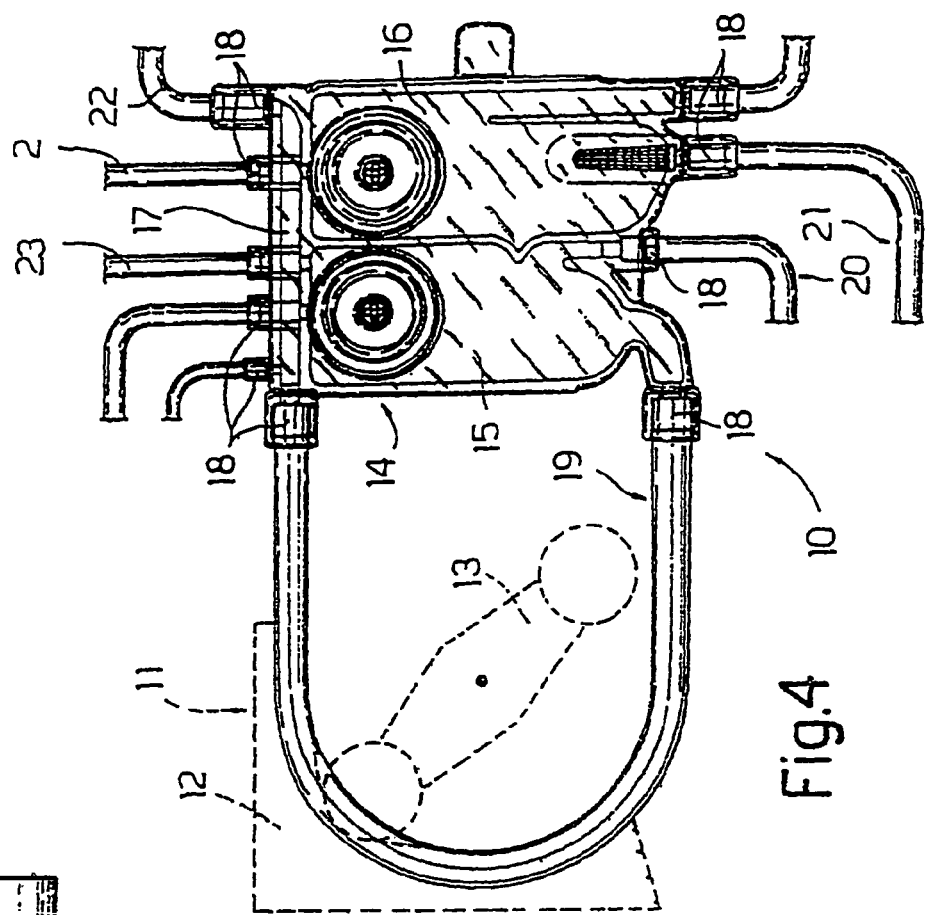
FIG. 4 is a side view in elevation, with parts removed for clarity, of an extracorporeal circuit for the circulation of blood in a machine for the purification of blood.

Now we refer to the embodiments of FIGS. 1 to 6.

With reference to FIG. 1, 1 illustrates a single-layer tube for medical applications manufactured by means of a process for the extrusion of a chlorine-free polymer which is soluble in a solvent having a solubility parameter within the range $9.9\pm1.5$ (cal/cm$^3$)$^{1/2}$, for example cyclohexanone.

Tube 1 has a single layer 2 which defines an outer surface 2a and an inner surface 2b of tube 1. If used to constitute a pump length, tube 1 has an inside diameter of between 6.0 and 8.5 mm and an outside diameter of between 9.0 and 13.0 mm. When tube 1 is used for normal lines which are not intended to act together with a peristaltic rotary pump, tube 1 has an inside diameter of between 0.41 and 8.5 mm and an outside diameter of between 3.25 and 13.00 mm.

In accordance with the embodiment illustrated, the polymer used for the manufacture of tube 1 is a low or high density thermoplastic polyurethane TPU. In particular, the thermoplastic polyurethane TPU is an aromatic polyester, to which wax may be added to reduce the friction of the outer surface 2a of tube 1.

A material which has proved suitable for manufacture of tube 1 described above is DESMOPAN KU-2 8670 manufactured by Bayer.

With reference to FIG. 2, 3 indicates a multilayer tube which is manufactured by coextrusion and comprises an outer layer 4 having a thickness between 50 μm and 100 μm (microns) of thermoplastic polyurethane TPU, and for example TEXIN® 5286 manufactured by Bayer®, which has a solubility parameter lying within the range $9.9\pm1.5$ (cal/cm$^3$)$^{1/2}$, has proved to be satisfactory.

Tube 3 comprises an inner layer 5 manufactured from polyolefin and elastomer and having a thickness of between 100 μm and 1960 μm (microns). The polyolefin is selected from polypropylene and polyethylene, while the elastomer is selected from SEPS and SEBS. Inner layer 5 has the function of conferring high resistance to kinking upon tube 3.

Tube 3 has an inner surface 5a and an outer surface 4a and incorporates an intermediate connecting layer 6 having a thickness which can vary between 20 and 100 microns. Connecting layer 6 comprises a polyolefin mixed with an elastomer and a polymer which has properties of adhesion to thermoplastic polyurethane TPU.

With reference to FIG. 3, a multilayer tube 7 manufactured by coextrusion comprises an outer layer 8 of thickness between 20 μm and 300 μm (microns) and an inner layer 9, of thickness between 100 μm and 2000 μm, which define an outer surface 8a and an inner surface 9a of tube 7 respectively. Outer layer 8 is manufactured from a SEBS-based compound whose trade name is CAWITON PR5026D manufactured by Wittenburg BV, the Netherlands, while the inner layer is manufactured from elastomer (SEBS) or polyolefin+elastomer (SEBS). Outer layer 8 of the said material thus has a solubility parameter within the range $9.9\pm1.5$ (cal/cm$^3$)$^{1/2}$ so that it is soluble in cyclohexanone. The compatibility between the materials of the outer layer and inner layer does not require the presence of a connecting layer.

Tubes 1, 3 and 7 are used to manufacture the corresponding parts of an extracorporeal circuit 10 for the circulation of blood illustrated in FIG. 4.

Figure 6:
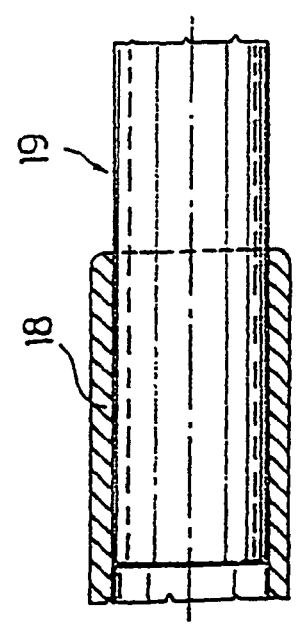
FIG. 6 is a side view in elevation, with parts removed for clarity and parts in cross section, of the tube and connector in FIG. 5 connected together.

Circuit 10 can be connected to a machine 11 for the purification of blood, a support 12 and a rotor 13 of a peristaltic pump of which are illustrated by dashed lines in FIG. 6. Circuit 10 comprises a rigid cassette 14 which is manufactured from PETG and defines two expansion chambers 15 and 16 and a duct 17. Cassette 14 incorporates a plurality of connectors 18 which are welded to the corresponding flexible tubes in circuit 10. The flexible tubes comprise a pump branch 19, a venous branch 21, an arterial branch 20, two branches 22 for connecting cassette 14 to a filter, not shown, and service branches 23, and are connected to corresponding connectors 18 of cassette 14 by means of a chemical joint using a solvent having a solubility parameter within the range $9.9\pm1.5$ (cal/cm$^3$)$^{1/2}$ with cyclohexanone.

Figure 5:
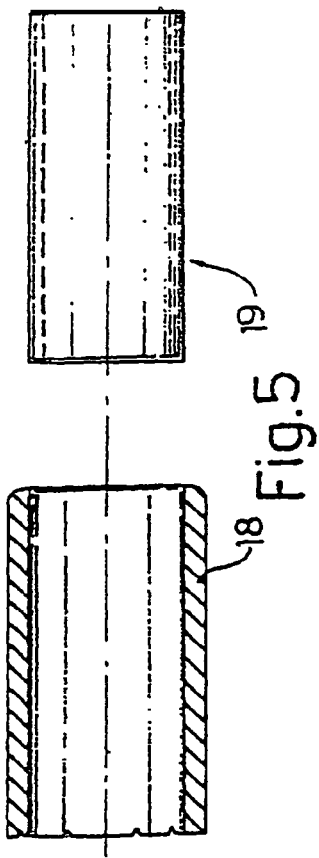
FIG. 5 is a side view in elevation, with parts removed for clarity and parts in cross section, of a tube constructed in accordance with this invention and a connector for the circuit in FIG. 4.

Pump branch 19 is manufactured using a single-layer tube 1 of thermoplastic polyurethane TPU and is welded to corresponding connector 18 through the application of cyclohexanone along a terminal portion of the outer surface of pump branch 19 as illustrated in FIG. 5. Subsequently the terminal portion of pump branch 19 is inserted into connector 18 manufactured from PETG. The cyclohexanone dissolves part of layer 2 corresponding to surface 2a and an internal portion of connector 18, thus forming an effective weld between length 19 and cassette 14.

Branches 20, 21, 22 and 23 are manufactured using tubes 3 having an outer layer 4, an inner layer 5 and a connecting layer 6 as described previously.

As an alternative, branches 20, 21, 22 and 23 are constructed from two-layer tubes 7 having an outer layer 8 and an inner layer 9 having the dimensions and properties already previously described.

Some examples of tubes 1, 3 and 7 used in the manufacture of circuit 10 are provided below.

EXAMPLE 1

Single-layer Tube Manufactured from Thermoplastic Polyurethane TPU.

The applicant has performed tests on welding between two types of tube 1 (indicated below as tube 1A and tube 1B) manufactured from thermoplastic polyurethane and a connector 18 manufactured from PETG. Tube 1 has the following dimensions:

Tube 1A

Inside diameter 4.17 mm—Outside diameter 6.55 mm

Tube 1B

Inside diameter 6.36 mm—Outside diameter 9.54 mm

The thermoplastic polyurethane TPU used to manufacture tubes 1A was TEXIN® 5286 manufactured by Bayer, while tube 1B was manufactured from a thermoplastic polyurethane, DESMOPAN KU 2-8670 manufactured by Bayer, to which wax was added as a lubricant.

The bond was produced by applying cyclohexanone to the outer surface 2a of tube 1 along an end portion of that tube 1. The portion was inserted into connector 18, which partly dissolved on contact with the cyclohexanone placed on the aforesaid portion.

Once the action of the solvent had ceased the applicant performed tensile and hydraulic leak tests which yielded satisfactory results.

Tube 1, especially in version 1B, has a relatively high kinking angle and relatively low friction which renders tube 1 particularly suitable for use as pump branch 19.

EXAMPLE 2

Multilayer Tube with an Outer Layer of Thermoplastic Polyurethane TPU.

The applicant has performed tests on welding between a tube 3 and a connector 18 manufactured from PETG.

Tube 3 had the following dimensions: Inside diameter 4.17 mm—Outside diameter 6.55 mm—Thickness of the outer layer 0.10 mm—Thickness of the inner layer 0.99 mm—Thickness of the connecting layer 0.10 mm.

The thermoplastic polyurethane TPU used to manufacture thermoplastic outer layer 4 was TEXIN® 5286 manufactured by Bayer.

Inner layer 5 was manufactured using a base material of CAVITON MED PR 4907 manufactured by Wittenburg BV—the Netherlands.

Connecting layer 6 was manufactured using a base material of CAWITON MED PR 5287 manufactured by the same Wittenburg.

The weld was made by applying cyclohexanone to the outer surface 4a of tube 3 along an end portion of that tube 3.

The portion was inserted into connector 18, which dissolved on contact with the cyclohexanone placed on that portion.

Once the action of the solvent had ceased the applicant carried out tensile and hydraulic leak tests on the weld which yielded satisfactory results.

The low kinking angle of tube 3 makes tube 3 suitable for the manufacture of branches 20, 21, 22.

Now we refer to the embodiments of FIGS. 7 to 10.

In FIG. 7, the number 1' indicates the whole of a blood circulation circuit for a blood purification machine M. The circuit 1' comprises an arterial branch 2', a venous branch 3' and a structure of rigid material, or casing, 4', which comprises an expansion chamber 5' located in the arterial branch 2', an expansion chamber 6' located in the venous branch 3' and a channel 7' located above the expansion chambers 5' and 6'.

The arterial branch 2' and the venous branch 3' comprise a plurality of tubes 8', each of which has two end portions 9' Each of the portions 9' can be joined (FIGS. 8 and 9) to a portion 12' of a connector 13' of the casing 4' or to a portion 10' of a connector 11' for connection to other members or devices or parts of the machine M not shown in detail.

The arterial branch 2' comprises a pump tube 14', which is curved in a U-shape around a rotor 15' of the machine M to form a peristaltic pump. The pump tube 14' comprises two end portions 16', each of which is welded to a portion 12' of a connector 13' of the casing 4' (FIG. 10).

The circuit 1' comprises additional tubes, again indicated by 8', used as vents or for taking off or introducing a fluid; one of the end portions 9' of each additional tube 8' is welded to a portion 12' of a connector 13' of the casing 4' and the other is welded to a portion 10' of a connector 11'.

The weld between one of the tubes 8' and one of the connectors 11' is produced at the portion 9' by the application of cyclohexanone, having a solubility parameter of 9.9 $(cal/cm^3)^{1/2}$ according to the ASTM D3132 standard, to the corresponding portion 9'. The portion 9' is then inserted into the connector 11', in contact with the corresponding portion 10'. The weld is produced as a result of the solubility in cyclohexanone of the materials forming the portions 9' and 10'.

In a similar way, the tubes 8' are welded to the connectors 13' of the casing 4' and the tube 14' is welded to the connectors 13' of the said casing 4'.

With reference to FIG. 8, this shows an example of a triple-wall tube. The tube 8' of FIG. 8 comprises an outer wall 17' having a thickness in the range from 50 µm (microns) to 100 µm, made from thermoplastic polyurethane (TPU); for example, a suitable TPU has been found to be that having the trade name of Texin® 5286, produced by Bayer, whose solubility parameter is advantageously within the range of 9.9±1.5 $(cal/cm^3)^{1/2}$. The tube 8' of FIG. 8 also comprises an inner wall 18', having a thickness in the range from 100 µm (microns) to 1960 µm, made from a combination of polyolefin and SEBS or SEPS, and an intermediate wall 19', having a thickness in the range from 20 µm (microns) to 100 µm, comprising polyolefin and SEBS.

With reference to FIG. 9, the tube 8' comprises an outer wall 20' having a thickness in the range from 20 µm (microns) to 300 µm, made from an SEBS-based compound having the trade name Cawiton PR5026D®, produced by Wittenburg, whose solubility parameter is advantageously within the range of 9.9±1.5 $(cal/cm^3)^{1/2}$, and an inner wall 21', having a thickness in the range from 100 µm (microns) to 2000 µm, made, for example, from a combination of polyolefin and SEBS.

In these two specific embodiments of the tubes 8' respectively, the outer wall 17' and the outer wall 20' form the portion 9', which, as indicated above, is the portion of the tube used to form the connection.

With reference to FIG. 10, the portion 16' of the tube 14' is a portion of single-wall tube having an external diameter in the range from 9.0 mm (millimetres) to 1.3 mm and an internal diameter in the range from 6.0 to 8.5 mm (millimetres). This portion 16' of the tube 14' is preferably made from thermoplastic polyurethane (TPU) whose trade name is Desmopan KU-2 8670, produced by Bayer, to which wax has been added as a lubricant.

It should be noted that if single-wall tubing is to be used for tubing other than the pump portion, the radial dimensions of such tubing can vary over the following ranges: internal diameter: 0.41 mm to 8.5 mm—external diameter: 3.25 mm to 13.00 mm.

The connectors 11' are preferably made from PETG or MBS or SEBS-based compounds, whose solubility parameters are also in the range from 8.4 $(cal/cm^3)^{1/2}$ to 11.4 $(cal/cm^3)^{1/2}$; in a possible variant, only the connecting portions 10' of the connectors 11' are made from PETG or MBS or SEBS-based compounds having solubility parameters in the range 9.9±1.5 $(cal/cm^3)^{1/2}$.

The connectors 13' of the casing 4' are made from PETG and, in a similar way to that mentioned in respect of the connectors 11', in a possible variant it is permissible to make only the connecting portions 10' of the connectors 11' from PETG.

Each of the chambers 5' and 6' is delimited by rigid walls, and has a corresponding pressure sensor PS, which, as shown in FIG. 7, comprises a membrane 22' made from elastomer. The membrane 22' is of circular shape and is welded by ultrasonic welding to the casing 4' made from PETG.

The circuit 1' also comprises two pinch devices 23', each engaging with a corresponding tube 8' and capable of interrupting or varying the flow of blood in the said tubes 8'. In particular, the pinch devices 23' are made from polyethylene.

Finally, the circuit 1' comprises two injection points 24', each of which is fitted in a corresponding connector 11' and is made from a latex-free elastomer.

The above example shows clearly the large number of welds present in the blood circulation circuit 1' of a blood purification machine, and consequently shows how important it is to use a polymer material capable of providing a hermetic seal between the first and the second components when a solvent is used.

Clearly, the present invention is not limited to the use of cyclohexanone as the solvent, but requires the selection of a solvent having a specified solubility parameter and the selection of the materials of the circuit from chlorine-free materials having solubility parameters within a range located in the vicinity of the solubility parameter of the solvent. The selection of the material having a specified solubility parameter can be limited to those portions that are involved in the welding.

The invention claimed is:

1. A blood circulation circuit comprising flexible components being made from a chlorine-free polymer material and including flexible tubes being made from a chlorine-free polymer material, each of said flexible tubes presenting at least one inner layer and one radially outer layer, the at least one inner layer being made from a combination of at least one polyolefin and at least one elastomer, the at least one radially outer layer being made from thermoplastic polyurethane, each of said flexible tubes presenting at least a corresponding end portion having said one inner and said one radially outer layers, said blood circulation circuit further comprising at least one rigid component being made from a chlorine-free polymer material and comprising a casing being made from a chlorine-free polymer material and second portions of said casing being made from a chlorine-free polymer material, the second portions of said at least one rigid component presenting one inner surface and one radially outer surface and being made from a material selected from the group consisting of PETG, MBS and SEBS-based compound, said PETG, MBS and SEBS-based compound being made from a chlorine-free polymer material and having a corresponding solubility parameter lying within a range of $9.9 \pm 1.5$ $(cal/cm^3)^{1/2}$, the radially outer layer of thermoplastic polyurethane of the end portions of said flexible tubes having a solubility parameter lying within a range of $9.9 \pm 1.5$ $(cal/cm^3)^{1/2}$ being hermetically sealed to the corresponding inner surface of the second portion of said casing made from a material selected from the group consisting of PETG, MBS and SEBS-based compound and having a solubility parameter lying within a range of $9.9 \pm 1.5$ $(cal/cm^3)^{1/2}$ so that the end portions of the flexible tubes and the second portions of the casing can be being joined together by means of a chemical joint using a solvent having a solubility parameter lying within said range.

2. A circuit according to claim 1, wherein said first and second portions have corresponding solubility parameters lying within a range from 9.4 to 10.4 $(cal/cm^3)^{1/2}$.

3. A circuit according to claim 1, wherein said first and second portions are soluble in a solvent comprising cyclohexanone.

4. A circuit according to claim 3, wherein said first portions of the flexible components are made from thermoplastic polyurethane.

5. A circuit according to claim 4, wherein said polyurethane is polyether-based.

6. A circuit according to claim 5, wherein said polyether is an aromatic polyether.

7. A circuit according to claim 4, wherein said first portions comprise at least one lubricant additive.

8. A circuit according to claim 1, wherein said flexible components also comprise a pump tube comprising two end portions each of which is fixed to a portion of a connector of said casing to form a portion designed to receive a rotor of a pump.

9. A circuit according to claim 8, wherein said pump tube is a single-wall tube made of one layer of TPU based material, said pump tube having an external diameter in the range from 9.0 mm to 13.0 mm and an internal diameter in the range from 6.0 mm to 8.5 mm, made entirely from a material having a solubility within the range of $9.9 \pm 1.5$ $(cal/cm^3)^{1/2}$.

10. A circuit according to claim 1, wherein said casing forms at least one chamber with rigid walls.

11. A circuit according to claim 1, wherein each of said tubes comprises at least three walls adjacent to each other, namely an outer wall having a thickness in the range from 50 μm to 100 μm, made from a polymer material having a solubility parameter lying within a range of $9.9 \pm 1.5$ $(cal/cm^3)^{1/2}$, said outer wall forming a corresponding first portion; an inner wall having a thickness in the range from 100 μm to 1960 μm, made from a combination of polyolefin and SEBS or SEPS; and an intermediate wall having a thickness in the range from 20 μm to 100 μm, said intermediate wall comprising polyolefin and SEBS.

12. A circuit according to claim 1, wherein said outer wall forms said first portion and has a thickness in the range from 20 μm to 300 μm, and said inner wall has a thickness in the range from 100 μm to 2000 μm, said outer wall being made from a polymer having a solubility parameter within the range $9.9 \pm 1.5$ $(cal/cm^3)^{1/2}$.

13. A circuit according to claim 1, wherein said first portions form outer walls of said flexible components.

14. A circuit according to claim 1, wherein said at least one polyolefin is selected from the group consisting of polyethylene and polypropylene, and said at least one elastomer is selected from the group consisting of SEPS and SEBS.

15. A circuit according to claim 1, wherein said casing forms at least one chamber with rigid walls, designed to hold a predetermined quantity of blood, said casing being made from a chlorine-free polymer material, having a solubility parameter lying in a solubility range of $9.9 \pm 1.5$ $(cal/cm^3)^{1/2}$;

the at least one radially outer wall being made from a chlorine-free polymer material having a solubility parameter lying in a range of $9.9 \pm 1.5$ $(cal/cm^3)^{1/2}$;

said flexible components further comprising at least one tube having opposite ends, the opposite ends being joined to corresponding connectors provided on said casing to form at least one U-shaped portion positioned so that said U-shaped portion can be coupled to a corresponding rotor of a pump, said tube comprising a single wall entirely made from a chlorine-free polymer material having a solubility parameter lying in a solubility range of $9.9 \pm 1.5$ $(cal/cm^3)^{1/2}$.

16. A blood circulation circuit comprising flexible components being made from a chlorine-free polymer material and including flexible tubes being made from a chlorine-free polymer material, each of said flexible tubes presenting at least a corresponding end portion, at least one of said flexible tubes presenting at least one inner layer and one radially outer layer, the at least one radially outer layer being made from thermoplastic polyurethane, said blood circulation circuit further comprising at least one rigid component being made from a chlorine-free polymer material and having a corresponding solubility parameter lying within a range of $9.9 \pm 1.5$ $(cal/cm^3)^{1/2}$, said rigid component presenting a casing being made from a chlorine-free polymer material, second portions being made from a chlorine-free polymer material and connectors being made from a chlorine-free polymer material, said flexible tubes further comprising at least one tube having opposed ends, the opposite ends being joined to corresponding connectors provided on said casing to form at least a U-shaped portion positioned so that the U-shaped portion can be coupled to a corresponding rotor of a pump, wherein the flexible tube including the U-shaped portion for the pump rotor is a single-layer tube made of thermoplastic polyurethane having a corresponding solubility parameter lying within a range of $9.9\pm1.5$ $(cal/cm^3)^{1/2}$ so that the end portions of the flexible tube and the connectors of the casing can be being joined together by means of a chemical joint using a solvent having a solubility parameter lying within said range, and wherein the flexible tubes presenting at least one inner layer and one radially outer layer define at least a venous branch and an arterial branch, at least the radially outer layer of their corresponding end portion being hermetically sealed to the second portions of the casing.

17. A blood circulation circuit according to claim 16, wherein the second portions of said at least one rigid component is made from a material selected from the group consisting of PETG, MBS and SEBS-based compound, said PETG, MBS and SEBS-based compound being made from a chlorine-free polymer material and having a corresponding solubility parameter lying within a range of $9.9\pm1.5$ $(cal/cm^3)^{1/2}$, the radially outer layer of thermoplastic polyurethane of the end portions of said flexible tubes having a solubility parameter lying within a range of $9.9\pm1.5$ $(cal/cm^3)^{1/2}$ being hermetically sealed to the corresponding the second portion of said casing made from a material selected from the group consisting of PETG, MBS and SEBS-based compound and having a solubility parameter lying within a range of $9.9\pm1.5$ $(cal/cm^3)^{1/2}$ so that the end portions of the flexible tubes and the second portions of the casing can be joined together by means of a chemical joint using a solvent having a solubility parameter lying within said range.

18. A blood circulation circuit according to claim 16, wherein the flexible tubes presenting at least one inner layer and one radially outer layer define at least two further branches for connecting the casing to a filter, at least the radially outer layer of their corresponding end portion being hermetically sealed to the second portions of the casing.

* * * * *